United States Patent [19]

Rogers

[11] Patent Number: 4,821,587
[45] Date of Patent: Apr. 18, 1989

[54] DEPTH GAUGE-ANALYZER

[76] Inventor: M. Maurice Rogers, Route 1, Box 214, Downsville, La. 71234

[21] Appl. No.: 17,737

[22] Filed: Feb. 24, 1987

[51] Int. Cl.⁴ .................... G01N 1/12; G01F 23/04
[52] U.S. Cl. ............... 73/864.63; 73/864.65; 73/864.66; 33/717
[58] Field of Search .......... 73/864.63, 864.65, 864.66; 33/126.4 R

[56] References Cited

U.S. PATENT DOCUMENTS

| | | | |
|---|---|---|---|
| 200,981 | 3/1878 | Cox | 73/864.63 |
| 832,164 | 10/1906 | Rutenber | 73/864.65 |
| 1,621,857 | 3/1927 | Seraphin | 73/864.65 |
| 1,769,533 | 7/1930 | Nash et al. | 73/864.65 |
| 2,203,019 | 6/1940 | Johnson et al. | 73/864.65 |
| 2,593,830 | 4/1952 | Baker | 73/864.65 |
| 3,169,322 | 2/1965 | Milo | 73/864.65 X |
| 3,379,065 | 4/1968 | Gibbon | 73/864.65 |
| 3,390,463 | 7/1968 | Hirsch | 73/864.5 X |
| 4,326,427 | 4/1982 | Uberschaer | 73/864.65 |

FOREIGN PATENT DOCUMENTS 24402 10/1907 United Kingdom .

Primary Examiner—Tom Noland
Attorney, Agent, or Firm—Hughes, Cassidy & Multer

[57] ABSTRACT

A telescopically collapsible depth gauge-analyzer which has one mode of operation that results in a sample being collected as the device is lowered through a body of the liquid of interest. In a second mode of operation, liquid is not allowed to flow into the device until it reaches the bottom of the body of liquid and an inlet valve in the bottom of the device is opened. The depth gauge-analyzer is equipped with an arrangement which allows the inlet valve to be opened and the collected liquid to be drained from the device without contacting the user. Visual and/or audible indicators make the user of the device aware that the liquid of interest is flowing into it and that the drawing of a sample has been completed.

19 Claims, 3 Drawing Sheets

U.S. Patent    Apr. 18, 1989    Sheet 1 of 3    4,821,587
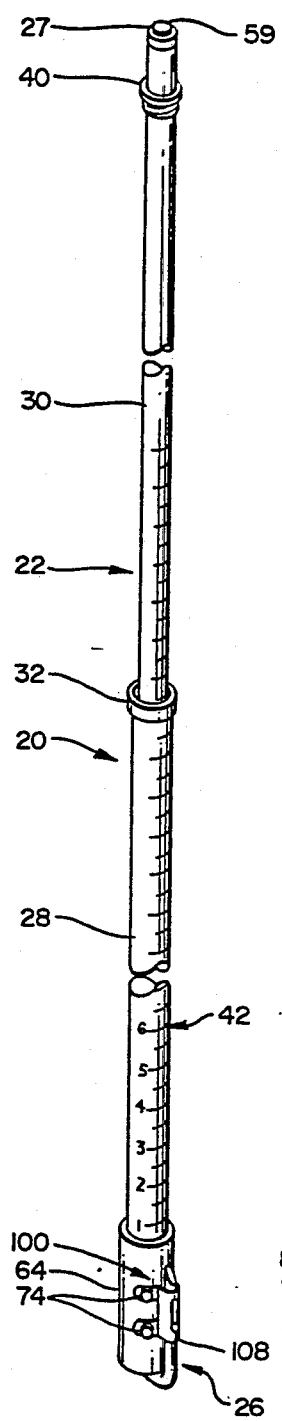
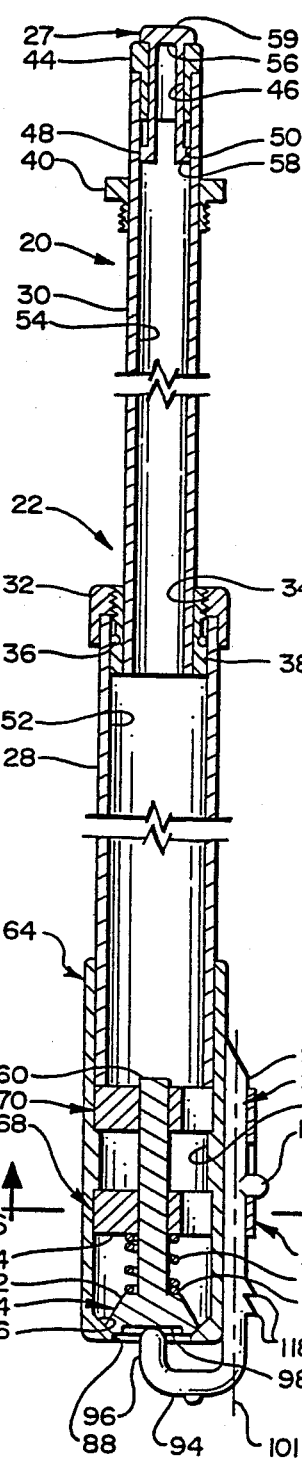
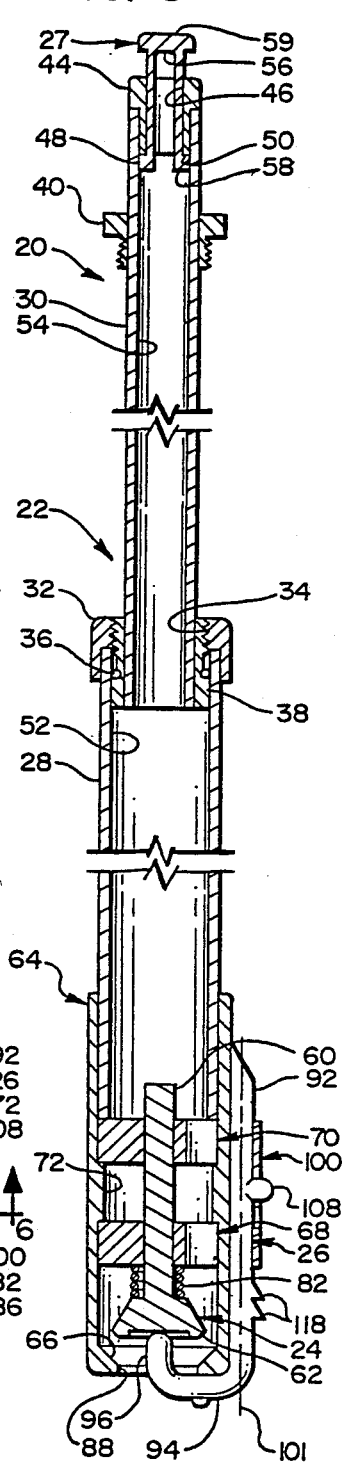

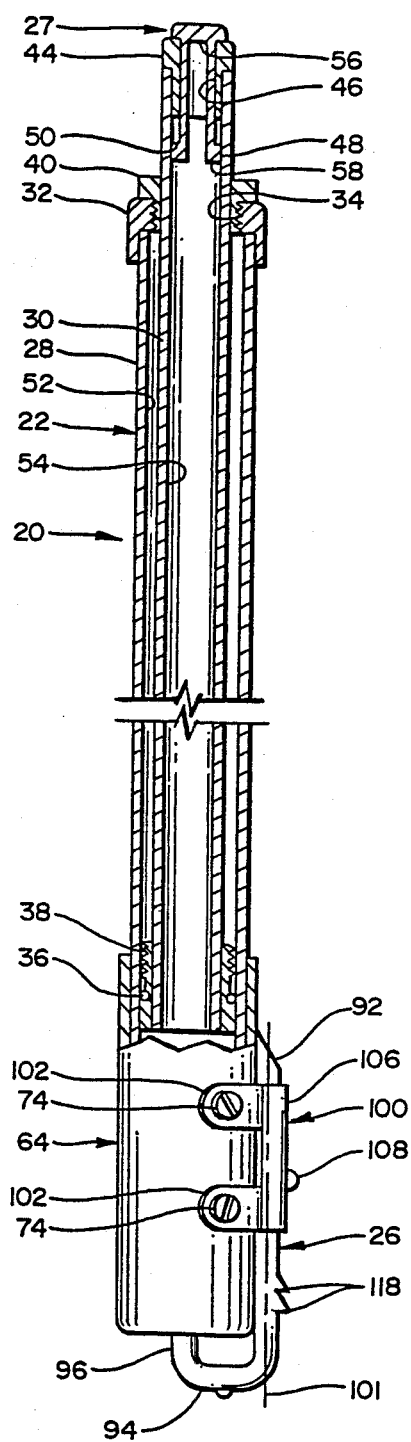
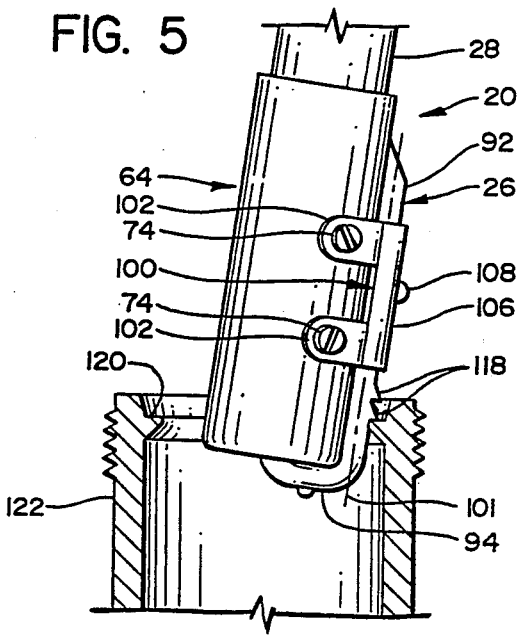
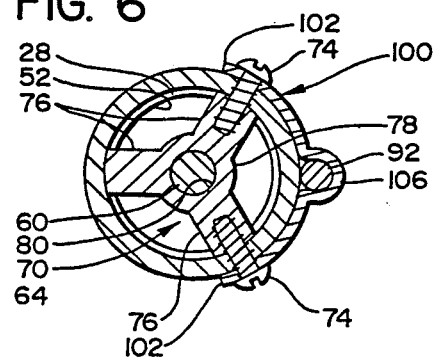

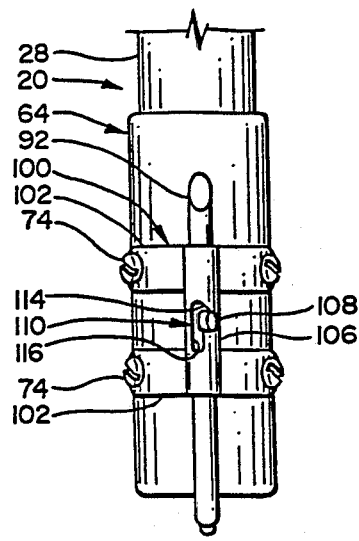
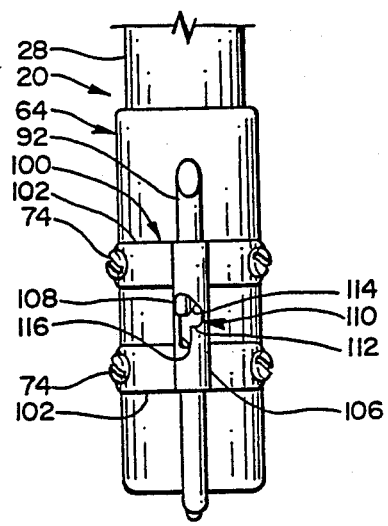
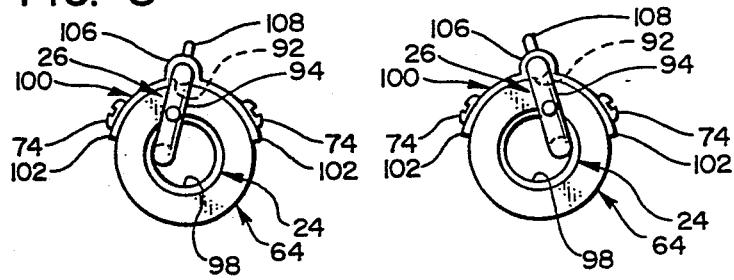
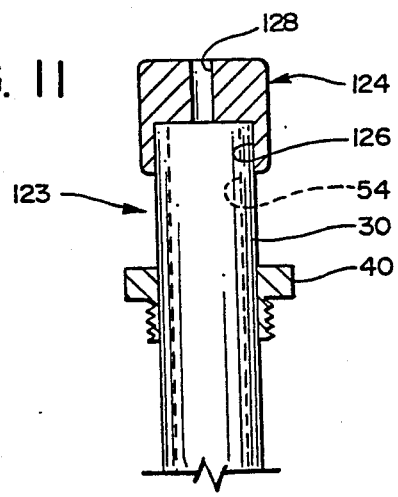

DEPTH GAUGE-ANALYZER

The present invention relates to novel, improved devices for measuring the depth of the liquid in a body of that liquid and for retrieving a sample of the liquid for analysis. Devices of that character will for the most part be referred to herein as depth gauge-analyzers.

BACKGROUND OF THE INVENTION

A continuing demand exists for simple, inexpensive, mechanical devices which can be used to measure the depth of a body of liquid and to retrieve samples from the body so that the presence of contaminants in that body and/or characteristics of the liquid can be ascertained. Such devices are commonly used to measure the amount of fuel remaining in a storage tank, to ascertain whether there is water and/or foreign substances in the storage tank, to measure the depth of water in ship's bilges, and for other purposes familiar to those to whom this specification is addressed.

Devices of the character just described which resemble mine to some limited extent in appearance and/or in the capabilities they possess have heretofore been proposed. Those of which I am aware are disclosed in U.S. Pat. Nos. 200,981 issued Mar. 5, 1878, to Cox for COMBINED HYDROMETER CUP AND THIEF; 832,164 issued Oct. 2, 1906, to Rutenber for CASK OR TANK GAGE; 1,621,857 issued Mar. 22, 1927, to Seraphin for AUTOMATIC TANK GAUGE; 1,769,533 issued July 1, 1930, to Nash et al. for GAUGE STICK; 2,203,019 issued June 4, 1940, to Johnson et al. for GAUGE; 2,593,830 issued Apr. 22, 1952, to Baker for LIQUID SAMPLER; 3,169,322 issued Feb. 16, 1965, to Milo for COMBINED GAGE AND SAMPLER DEVICE; and 3,390,463 issued July 2, 1968, to Hirsch for LIQUID-LEVEL GAGE and in 1906 British patent specification No. 24,402 (Adamson).

For the most part, the patent documents identified in the preceding paragraph disclose devices which include an elongated tube or barrel with a spring biased valve at its lower end. Pressing the device against the bottom of a receptacle containing the liquid of interest opens the valve, allowing the liquid to flow into the tube until the level of liquid in the tube is the same as the liquid level in the receptacle. The subsequent release of downward pressure on the device allows a cooperating spring to close the valve, trapping the thus sampled liquid in the tube. That component is typically fabricated from a transparent material, allowing the operator to visually check for foreign substances in the liquid of interest.

In many instances, the contaminant may be present as a separate layer; and the existence, location, and thickness of the layer may be items of importance. Stratification cannot be maintained when a device as just described is employed to draw a sample because of the relative movement between the contaminant and the liquid of interest that inevitably occurs as the liquid and contaminant flow upwardly into the sampling tube of the device through the valve in its lower end.

Baker U.S. Pat. No. 2,593,830 does disclose a liquid sampling device which eliminates the just-discussed problem because the valve of that device is latched open until the device reaches the bottom of the receptacle and the latch is tripped. However, the Baker device lacks versatility in that there is no provision for first lowering the device and then opening the valve when the bottom of the body of liquid is reached as is desirable when it is those impurities at the very bottom of the liquid containing receptacle that are of interest.

Another disadvantage of heretofore proposed devices of the character in question is that the actuator is located beneath the liquid inlet and drain opening in the valve seat and must be displaced upwardly to open the valve and drain the sample from the tube. If the operator does this with his hand, the escaping liquid may soil him or cause even more severe problems if the liquid is corrosive, for example.

On the other hand, this heretofore employed location of the valve actuator does not lend itself to positioning the tube over an access opening and then opening the valve to drain the liquid back into the receptacle from which it was drawn unless the operator does use his hand to open the valve. There is nothing against which the valve actuator can be butted to displace it and thereby open the valve.

Another common deficiency of heretofore available liquid sampling devices is the absence of a visual, audible, or other indication to the operator that the flow of liquid into the tube of the sampling device has ceased and that the taking of the sample is therefore complete. The advantage of such an indication is important and self-evident.

SUMMARY OF THE INVENTION

I have now invented, and disclosed herein, certain novel, improved depth gauge-analyzers which do not have the above-discussed drawbacks common to those heretofore disclosed liquid samplers of which I am aware.

My novel depth gauge-analyzers differ from those of which I am aware in one respect in that they have an inlet valve which can be latched open or allowed to remain closed at the operator's option while the device is lowered through the body of liquid being sampled. As a consequence, the operator can elect to draw a sample which is stratified or otherwise composed in the same manner as the liquid in the subject body or a sample which is primarily composed of contaminants from the bottom of the body of liquid.

Also, in my novel gauge-analyzers, the inlet valve actuator has a section which lies to one side of the device's tube and includes a catch that can be engaged to displace the actuator in a valve-opening direction. As a consequence, the device can be drained by positioning the bottom end of the tube over an inlet opening to the receptacle containing the liquid being evaluated and then engaging the catch on the rim of that opening and pressing the tube in a downward direction. This displaces the actuator, opening the inlet valve and draining the liquid sample into the receptacle.

Yet other important, practical features of the novel depth gauge-analyzers disclosed herein are visual and audible indicators which allow the operator to confirm that: (1) the sampled liquid is flowing into the sampling tube of the device, and (2) the flow has ceased and the taking of the sample has therefore been completed.

Also, the novel liquid depth gauge-analyzers disclosed herein are of a telescopible or collapsible construction which makes them significantly easier to handle and store than those of the one-piece construction heretofore typically employed.

A liquid sampling device of collapsible construction is proposed in above-cited Hirsch U.S. Pat. No. 3,390,463. However, the Hirsch device employs an arrangement which is significantly inferior to mine as far as its ability to maintain the two sections of that device's barrel in a wanted, collapsed or extended relationship is concerned. This is important from the standpoint of accuracy when a depth measurement is being made and from the viewpoints of easy handling and protection against the damage that might occur during handling if one section of the Hirsch barrel slipped relative to the other one.

Aside from the foregoing, my novel devices are simple, durable, accurate, and relatively inexpensive to manufacture.

OBJECTS OF THE INVENTION

From the foregoing, it will be apparent to the reader that one important and primary object of my invention resides in the provision of novel, improved mechanical devices for measuring the depth of a body of liquid and for withdrawing from that body a sample which can be visually inspected or otherwise analyzed.

Other also important but more specific objects of the invention reside in the provision of depth gauge-analyzers as described in the preceding paragraph which:

allow the sample to be taken as the device is lowered through the body of liquid or after it has been lowered to the bottom of that body at the option of the operator;

allow the sample to be drained from the device easily and without creating a mess or contacting the operator;

provide an indication to the operator while the sample is being taken and/or an indication that the drawing of the sample has been completed;

can be telescoped or collapsed to facilitate their handling and storage;

are durable, simple, accurate, and relatively inexpensive to manufacture.

Other important objects and features and additional advantages of my invention will become apparent to the reader from the foregoing and the appended claims and as the ensuing detailed description and discussion proceeds in conjunction with the accompanying drawing.

BRIEF DESCRIPTION OF THE DRAWING

In the drawing:

FIG. 1 is a pictorial view of a telescopible depth gauge-analyzer constructed in accord with the principles of the present invention and extended to permit the taking of a sample;

FIG. 2 is a vertical section through the depth gauge-analyzer of FIG. 1 with an inlet valve at its lower end closed to retain a sample therein;

FIG. 3 is a view similar to FIG. 2 but with the valve opened to drain the sample from the depth gauge-analyzer;

FIG. 4 is a view similar to FIGS. 2 and 3 but with the depth gauge-analyzer telescoped to facilitate handling and storage;

FIG. 5 shows, pictorially, how the valve at the lower end of the depth gauge-analyzer can be expeditiously opened to drain a sample therefrom;

FIG. 6 is a section through the depth gauge-analyzer, taken substantially along line 6—6 of FIG. 2 to show one of two, virtually identical, vertically spaced apart guides for the liquid inlet valve at the lower end of the depth gauge-analyzer;

FIG. 7 is an elevation of the lower part of the depth gauge-analyzer, showing the actuator for the inlet valve and a latch arrangement which cooperates with the actuator to maintain the valve in the open position shown in FIG. 3;

FIG. 8 is a bottom view of the depth gauge-analyzer with the valve actuator in the latched, "valve open" position;

FIG. 9 is a view similar to FIG. 7 but with the valve actuator unlatched so that the valve can return to the closed position shown in FIG. 2;

FIG. 10 is a view similar to FIG. 8 but with the valve actuator in the unlatched position shown in FIG. 9; and FIG. 11 is a fragmentary elevation of a second embodiment of my invention which includes a whistle activated while a sample is being drawn to indicate to the user that liquid is collecting in the device.

DETAILED DESCRIPTION OF THE INVENTION

Referring now to the drawing, FIGS. 1–3 depict, in its extended or operative configuration, a depth gauge-analyzer 20 constructed in accord with, and embodying, the principles of the present invention.

Major components of depth gauge-analyzer 20 include: a collapsible or telescoping barrel 22, a valve 24 for controlling the flow of liquid being sampled into and out of depth gauge-analyzer barrel 22, an actuator 26 for valve 24, and a telltale 27. That component provides one indication to the user of depth gauge-analyzer 20 that the liquid being sampled is flowing into barrel 22 and a second indication that the drawing of a sample has been completed.

As is shown in FIGS. 1–4, barrel 22 has an elongated, lower, outer tube or section 28 and an inner, upper tube or section 30. Inner tube 30 is rectilinearly displaceable in lower tube 28 between the extended, operating relationship with tube 28 shown in FIGS. 1–3 and the collapsed or telescoped relationship shown in FIG. 4. As indicated above, the collapsed configuration facilitates the handling and storage of depth gauge-analyzer 20.

An internally threaded fitting 32 is fixed to, and forms a closure at, the upper end of lower or outer barrel section 28. The upper section 30 of the barrel slidably extends through a central bore 34 in that fitting. An 0-ring seal 36 surrounding and supported by fitting 32 and engaging the inner surface of lower barrel section 28 keeps liquid collected in barrel 22 from escaping through the gap between barrel sections 30 and 28.

A first, externally threaded, complementary fitting 38 is fixed to the lower end of inner barrel section 30; and a second, also complementary, externally threaded fitting 40 is fixed to inner barrel section 30 adjacent its upper end.

With the two barrel sections 30 and 28 in the extended, operating relationship shown in FIGS. 1–3, the lower complementary fitting 38 is threaded into the fitting 32 at the upper end of lower barrel section 28. That positively locks the two barrel sections together in the extended, operating relationship, insuring that the depth indicated by the scale 42 spanning barrel sections 28 and 30 accurately reflects the actual depth of the liquid in the body being sampled.

Barrel sections 30 and 28 will typically be fabricated of a clear engineering plastic. This allows the level of liquid in barrel 22 to be readily ascertained. It also allows the sample to be visually inspected for contaminants such as water and particulates.

When the two barrel sections 30 and 28 are collapsed as shown in FIG. 4 to facilitate handling and storage, the fitting 40 toward the upper end of inner barrel section 30 is threaded into the fitting 32 a the upper end of lower barrel section 28 as is shown in the just-mentioned figure. This positively locks the two barrel sections 30 and 28 together in the illustrated, telescoped relationship. As a consequence, the inner barrel section 30 is kept from sliding out of the outer barrel section 28. This is desirable from the viewpoint of handling and in protecting depth gauge-analyzer 20 from the damage that might be incurred if the two barrel sections 30 and 28 did slide apart while the depth gauge-analyzer was being handled.

Referring now most particularly to FIGS. 2 and 3, a shouldered closure member 44 is fixed in the upper end of inner barrel section 30. The above-briefly mentioned visual indicator or telltale 27 is slidably mounted in a central bore 46 through closure member 44 for rectilinear movement between the inactive position shown in FIG. 2 and the active position shown in FIG. 3. In its active position, telltale 27 indicates to the user of depth gauge-analyzer 20 that liquid is flowing into, and collecting in, the barrel 22 of the depth gauge-analyzer.

Telltale 27 is retained in the upper section 30 of barrel 22 by an integral, annular flange 48 which is engageable with the lower end 50 of shouldered fitting 54.

As the barrel 22 of depth gauge-analyzer 20 fills with the liquid being sampled, the volume above the collected liquid in the hollow interiors 52 and 54 of barrel sections 28 and 30 decreases. That raises the pressure on the air in those sections of barrel 22. The consequence is the generation of sufficient force on the annular, downwardly facing surfaces 56 and 58 of the telltale to elevate that component from the position shown in FIG. 2 to that shown in FIG. 3. This lets the user know that liquid is flowing into the tube.

Once the liquid being sampled has ceased to flow into the barrel 22 of depth gauge-analyzer 20, air will leak from the interiors 52 and 54 of barrel sections 28 and 30 and reduce the air pressure in barrel 22 to a level at which the telltale will return to the FIG. 2 position. This indicates to the user of depth gauge-analyzer 20 that the collection of the sample has been completed and that device 20 can accordingly be removed from the body of liquid being sampled.

To keep the pressure in the interiors 52 and 54 of barrel sections 28 and 30 from increasing to a level which would interfere with the flow of liquid into depth gauge-analyzer barrel 22 while providing sufficient pressure to operate telltale 27, one or more vents can be provided in the head 59 of the telltale or in the upper end of inner barrel section 30 below the flange 48 of the telltale. Such vents are commonly provided as is apparent from above-cited Seraphin U.S. Pat. NoS. 1,621,857; Nash et al. 1,769,533; and British patent specification No. 24,402. In view of this and the fact that the precise location and details of the vent(s) are not part of the present invention, vents have not been shown in the appended drawing.

Referring now in particular to FIGS. 2, 3, and 6, the valve 24 which controls the flow of liquid into and out of the barrel 22 of depth gauge-analyzer 20 includes an integral stem 60 and a valve head 62. Valve 24 is supported in a tubular closure member 64 (also preferably fabricated of a clear plastic) fixed to the lower end of outer depth gauge-analyzer barrel section 28 for movement toward and away from an integral valve seat 66 by two essentially identical guides or spiders 68 and 70. These spiders are fixed to closure member 64 in abutting relationship to the upper and lower surfaces of an annular shoulder 72 in the closure member as by screws 74 (see FIG. 6).

Each of the two spiders 68 and 70 has three, integral, equiangularly related legs 76 and a hub 78 with a central bore 80 through which valve stem 60 extends.

Valve 24 is biased toward valve seat 66; i.e., to the closed position shown in FIG. 2, by a coil spring 82. That spring surrounds valve stem 60 and extends between the bottom side 84 of the lower valve-guiding spider 68 and an annular ledge 86 at the top of valve head 62. In this closed position of valve 24, its head 62 blocks a central aperture 88 through valve seat 66. Liquid can, accordingly, neither flow into or out of the barrel 22 of depth gauge-analyzer 20 when valve 24 is in the closed, FIG. 2 position.

Valve 24 is moved away from valve seat 66 to allow the liquid being sampled to flow into depth gauge-analyzer barrel 22 and to allow the sampled liquid to drain therefrom by an actuator 26 as was mentioned above. This actuator is shown in FIGS. 1-5 and 7-10.

Actuator 26 has a J-shaped configuration. It includes a vertically extending, external leg 92; an integral leg 94 extending transversely across the bottom of depth gauge-analyzer 20 from leg 92; and an also integral, vertically extending, inner leg 96. The latter is aligned along the same vertical axis as valve member 24 and is seated in a recess 98 formed in the bottom of valve head 62.

Valve actuator 26 is supported from the closure member 64 at the lower end of depth gauge-analyzer 20 by a generally H-shaped bracket or keeper 100 for vertical, bidirectional, rectilinear movement and for rotation about a vertical axis 101. As is best shown in FIGS. 4-10, bracket 100 has four legs 102. The screws 74 by which spiders 68 and 70 are attached to closure member 64 extend through these legs and also fix the bracket to the closure member.

Bracket 100 can be fabricated of a suitable metal or of an appropriate engineering plastic.

The external, vertically extending leg 92 of actuator 26 is housed in, and trapped against, closure member 64 by an integral, generally U-sectioned flange or projection 106 which extends the length of mounting bracket 100. As is apparent from the drawing, this leaves actuator 26 free to rotate about axis 101 in mounting flange 106 and to move up and down in the bracket.

It was pointed out above that depth gauge-analyzer 20 permits two distinctly different methods of collecting a liquid sample to be employed. In the first of these, valve member 24 remains closed until: (1) the lower end of the depth gauge-analyzer reaches the bottom of the body of liquid being sampled, (2) the transverse leg 94 of actuator 26 engages the surface bounding the lower side of that body of liquid, and (3) the depth gauge-analyzer is then displaced further in a downward direction until the bottom end of closure member 64 reaches the transverse actuator leg 94. As shown in FIG. 3, this results in the inner, vertically extending actuator leg 96 displacing valve member 24 upwardly against the bias exerted by spring 82.

This allows liquid to flow first into the lower section 28 and then into the upper section 30 of depth gauge-analyzer barrel 22 through the opening 88 in valve seat 66. As was also discussed above, the liquid thus flowing into barrel 22 compresses the air in that barrel above the incoming liquid. That displaces telltale 27 to the FIG. 3 position, thereby indicating to the user that the depth gauge-analyzer barrel 22 is filling with liquid.

Once the level of the liquid in barrel 22 has reached that in the body of liquid being sampled, the inflow of liquid will cease; the air pressure in barrel 22 will decrease; and telltale 27 will return to the FIG. 2 position. That indicates to the user that the collection of the sample has been completed and that the depth gauge-analyzer can therefore be removed from the body of liquid being sampled. When this is done, spring 82 returns valve 24 to the closed position shown in FIG. 2. This prevents collected liquid from escaping from the depth gauge-analyzer barrel 22 through the opening 88 in valve seat 66.

In a second mode of operation, actuator 26 is latched in the position shown in FIG. 3 so that the liquid being sampled can flow into the barrel 22 of depth gauge-analyzer 20 as the latter is lowered through the body of liquid being sampled. Latching is accomplished by a mechanism which includes a latch 108 fixed to the outer, vertically extending leg 92 of valve actuator 26 and a cooperating, latch receiving opening 110 in actuator mounting bracket 100.

To latch actuator 26 with valve member 24 in the open, FIG. 3 position, the actuator 26 is displaced upwardly relative to closure member 64 and then rotated in a counterclockwise direction as shown in FIGS. 7 and 9 until the latch is seated on a horizontal ledge 112 at one side of opening 110. Valve member biasing spring 82 thereafter traps latch 108 against that ledge, thus keeping that spring from moving valve 24 to its closed, FIG. 2 position.

Once the wanted sample has been collected, downward pressure on depth gauge-analyzer barrel 22 followed by a release of that pressure will result in latch 108 moving upwardly off of ledge 112 and being guided along an inclined edge surface 114 at the upper end of opening 110 to the position shown in FIG. 9. Thereafter, as the depth gauge-analyzer 20 is removed from the body of liquid being sampled, latch 108 can travel down the vertically elongated part 116 of opening 110. This allows spring 82 to displace actuator 26 downwardly to the position shown in FIG. 2 and thereby close valve member 24.

As discussed above, this mode of operating depth gauge-analyzer 20 can be employed to advantage to collect a sample which accurately reflects the constitution of the body of liquid being sampled as far as stratification of liquids and distribution of contaminants in that body of liquid is concerned.

I pointed out above that another significant feature of the present invention is an arrangement which allows collected liquid to be drained from depth gauge-analyzer 20 without the user being required to handle the depth gauge-analyzer in a manner which might involve contact with the collected liquid.

The arrangement in question, best shown in FIGS. 2-5, includes integral projections or catches 118 on the vertically extending, exterior leg 92 of valve actuator 26. As is shown in FIG. 5, an appropriate one of these projections 118 can be engaged with, for example, the annular flange 120 typically found at the upper end of a liquid inlet or filler tube 122 for a liquid storage tank (not shown). Subsequently pressing depth gauge-analyzer barrel 22 downwardly displaces valve actuator 26 from its FIG. 2 position to its FIG. 3 position. That opens valve 24 and allows the collected liquid to drain back into the storage tank from the barrel 22 of the depth gauge-analyzer without contacting the user of the depth gauge-analyzer.

As was suggested above, a visual indicator such as telltale 27 may be replaced with an audible indicator if desired. This modification of the just-described embodiment of my invention is illustrated in FIG. 11.

The depth gauge-analyzer 123 illustrated in that figure is identical to the depth gauge-analyzer 20 described above except that the shouldered closure member 44 of the latter is replaced with a closure member 124 having a downwardly opening recess 126 in which the upper end of inner barrel section 30 is seated and fixed.

An appropriately sized orifice 128, akin to that found in the common whistling teakettle, extends through closure member 124 and communicates with the chamber or passage 54 in barrel section 30. With liquid flowing into the barrel of depth gauge-analyzer 123, the air in the barrel above that liquid is compressed. As the compressed air escapes through orifice 128, it generates a whistling sound, again indicating to the user of the depth gauge-analyzer that liquid is collecting in the barrel 22 of that device. Once the inflow of liquid has ceased, the pressure in passage 54 will drop; and the whistling sound will cease, letting the user of the depth gauge-analyzer know that the collection of the sample has been completed.

As will be apparent to those skilled in the arts to whom this specification is addressed, orifice 128 could equally well be formed through the head 59 of a telltale such as that identified by reference character 27 in FIGS. 2 and 3. This modification of my invention advises the user of depth gauge-analyzer 20 both audibly and visually that liquid is flowing into the barrel 22 of that device and that the inflow of the sampled liquid has been completed.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description; and all changes which come within the meaning and range of equivalency of the claims are therefore intended to be embraced therein.

What I claim as my invention is:

1. A device for measuring the depth of a body of liquid and for collecting a sample of said liquid, said device comprising: an elongated barrel having an upper end and a lower end in its operative orientation; an aperture valve seat forming a closure at the lower end of said barrel; a valve member; means biasing said valve member toward said valve seat to prevent the flow of liquid through said aperture; an actuator engageable with a surface at the bottom of said body of liquid and thereafter effective upon downward movement of said barrel to displace said valve member away from said valve seat and allow liquid to flow from said body into said barrel through said aperture; and means operable upon rotation of said actuator by the operator of said device about an axis paralleling the axis of elongation of said barrel to latch said actuator in a position in which it holds said valve member away from said valve seat, whereby liquid can flow into said barrel through said aperture as said device is lowered through said body of liquid.

2. A device for measuring the depth of a body of liquid and for collecting a sample of said liquid, said device comprising: an elongated barrel having an upper end and a lower end in the operative position thereof and valve means in the lower end of said barrel for controlling the flow of liquid into and out of said barrel; said barrel comprising: a first, elongated, outer tube; a second, elongated, inner tube rectilinearly and telescopically displaceable in said outer tube; a seal between said first and second tubes for preventing liquid from escaping through the gap therebetween; and means for coupling said first and second tubes together in a first, collapsed relationship and in a second, extended relationship, said last-mentioned means comprising: an internally threaded fitting fixed to said outer tube at the upper end thereof; a first, complementary, externally threaded fitting fixed to said inner tube at the lower end thereof; and a second, complementary, externally threaded fitting fixed to said inner tube toward the upper end thereof.

3. A device as defined in claim 2, wherein said seal surrounds, and is carried by, said first, externally threaded fitting.

4. A device for measuring the depth of a body of liquid and for collecting a sample of said liquid, said device comprising: an elongated barrel having an upper end and a lower end in the operative position thereof; valve means at the lower end of said barrel which can be opened to allow liquid to flow into and collect in said barrel; and pressure activated means operable while said liquid is flowing into said barrel for indicating to the user of said device that liquid is collecting therein.

5. A device as defined in claim 4 wherein said indicating means comprises means for providing a visual indication to the user of the device.

6. A device as defined in claim 4 which includes a centrally aperture closure member at the upper end of said barrel and wherein said indicating means comprises a rectilinearly displaceable telltale extending through the aperture in said closure member and trapped in said barrel by said closure member.

7. A device as defined in claim 4 wherein said indicating means comprises a whistle-incorporating closure member fixed to the upper end of said barrel.

8. A device for measuring the depth of a body of liquid and for collecting a sample of said liquid, said device comprising: an elongated barrel having an upper end and a lower end in its operative orientation; an aperture valve seat forming a closure at the lower end of said barrel; a valve member; means biasing said valve member towards said valve seat to prevent the flow of liquid through said aperture; an actuator engageable with a surface at the bottom of said body of liquid and thereafter effective upon downward movement of said barrel to displace said valve member away from said valve seat and allow liquid to flow from said body into said barrel through said aperture; and means operable by the operator of said device to latch said actuator in a position in which it holds said valve member away from said valve seat, whereby liquid can flow into said barrel through said aperture as said device is lowered through said body of liquid, said valve actuator having an external portion extending upwardly along the outer surface of said barrel and said device further including a keeper cooperating with said barrel to support said external portion of said actuator for rotation about a vertically extending axis and a latch member with said external portion of said actuator, there being an opening in said keeper through which said latch extends and said opening having a portion into which said latch can be displaced by rotation of said actuator portion to prevent said biasing means from displacing said valve member toward said valve seat, thereby allowing said liquid to flow into said barrel through said aperture as aforesaid as said device is lowered through said body of liquid.

9. A device for measuring the depth of the body of liquid and for collecting a sample of said liquid, said device comprising: an elongated barrel having an upper end and a lower end in its operative orientation; an aperture valve seat forming a closure at the lower end of said barrel; a valve member; means biasing said valve member toward said valve seat to keep liquid from flowing through said aperture; an actuator engageable with a surface at the bottom of said body of liquid and thereafter effective upon downward movement of said barrel to displace said valve member away from said valve seat and allow said liquid to flow into said barrel through said aperture; said actuator including means lying out of the plane of vertical projection of the bottom end of said barrel which can be manually engaged to so displace said actuator as to move said valve member away from said valve seat and allow liquid collected in said barrel to drain therefrom through the aperture in the valve seat; and said device further comprising means operable by the operator of said device to latch said actuator in a position in which it holds said valve member away from said valve seat, whereby liquid can flow into said barrel through said valve seat aperture as said device is lowered through said body of liquid, said valve actuator having an external portion extending upwardly along the outer surface of said barrel, and said device further including a keeper cooperating with said barrel to support said external portion of said actuator for rotation about a vertically extending axis and a latch with said external portion of said actuator, there being an opening in said keeper through which said latch extends and said opening having a portion into which said latch can be displaced by rotation of said actuator portion to prevent said biasing means from displacing said valve member toward said valve seat, thereby allowing said liquid to flow into said barrel through said aperture as aforesaid as said device is lowered through said body of liquid.

10. A device for measuring the depth of a body of liquid and for collecting a sample of said liquid, said device comprising an elongated barrel having an upper end and a lower end in its operative orientation; an aperture valve seat forming a closure at the lower end of said barrel; a valve member; means biasing said valve member toward said valve seat to keep liquid from flowing through said aperture; an actuator engageable with a surface at the bottom of said body of liquid and thereafter effective upon downward movement of said barrel to displace said valve member away from said valve seat and allow said liquid to flow into said barrel through said aperture; said actuator including means lying out of the plane of vertical projection of the bottom end of said barrel which can be manually engaged to so displace actuator as to move said valve member away from said valve seat and allow liquid collected in said barrel to drain therefrom through the aperture in the valve seat; and said device further comprising means operably by the operator of said device to latch said actuator in a position in which it holds said valve member away from said valve seat, whereby liquid can flow into said barrel through said valve seat aperture as said device is lowered through said body of liquid, the elongated barrel of said device comprising: a first elongated, outer tube, a second, elongated, inner tube rectilinearly and telescopically displaceable in said first tube; a seal between said first and second tubes for preventing liquid from escaping through the gap therebetween; and means for coupling said first and second tubes together in a first, collapsed relationship and in a second, extended relationship, said last-mentioned means comprising: an internally threaded fitting fixed to said outer tube at the upper end thereof; a first, complementary, externally threaded fitting fixed to said inner tube at the lower end thereof; and a second, complementary, externally threaded fitting fixed to said inner tube toward the upper end thereof.

11. A device as defined in claim 10 wherein said seal surrounds, and is carried by, said first, externally threaded fitting 12. A device for measuring the depth of a body of liquid and for collecting a sample of said liquid, said device comprising: an elongated barrel having an upper end and a lower end in its operative orientation; an aperture valve seat forming a closure at the lower end of said barrel; a valve member; means biasing said valve member toward said valve seat to keep liquid from flowing through said aperture; an actuator engageable with a surface at the bottom of said body liquid and thereafter effective upon downward movement of said barrel to displace said valve member away from said valve seat and allow said liquid to flow into said barrel through said aperture; said actuator including means lying out of the plane of vertical projection of the bottom end of said barrel which can be manually engaged to so displace said actuator as to move said valve member away from said valve seat and allow liquid collected in said barrel to drain therefrom through the aperture in the valve seat; and said device further comprising means operable by the operator of said device to latch said actuator in a position in which it holds said valve member away from said valve seat, whereby liquid can flow into said barrel through said valve seat aperture as said device is lowered through said body of liquid, and a pressure activated means operable while liquid is flowing into said barrel for indicating to the operator of said device that liquid is collecting therein.

13. A device as defined in claim 12 wherein said indicating means comprises means for providing a visual indication to the operator.

14. A device as defined in claim 12 which includes a centrally apertured closure member at the upper end of said barrel and wherein said indicating means comprises a rectilinearly displaceable telltale extending through the aperture in said closure member and trapper in said barrel by said closure member.

15. A device as defined in claim 12 wherein said indicating means comprises a whistle-incorporating closure member fixed to the upper end of said barrel.

16. A device for measuring a depth of a body of liquid and for collecting a sample of said liquid, said device comprising: an elongated barrel having an upper end and a lower end in its operative orientation; an apertured valve seat forming a closure at the lower end of said barrel; a valve member; means biasing said valve member toward said valve seat to keep liquid from flowing through said aperture; and actuator engageable with a surface at the bottom of said body of liquid and thereafter effective upon downward movement of said barrel to displace said valve member away from said valve seat and allow said liquid to flow into said barrel through said aperture; said actuator including means lying out of the plane of vertical projection of the bottom end of said barrel which can be manually engaged to so displace said actuator as to move said valve member away from said valve seat and allow liquid collected in said barrel to drain therefrom through the aperture in the valve seat; and said device further comprising means operably by the operator of said device to latch said actuator in a position in which it holds said valve member away from said valve seat, whereby liquid can flow into said barrel through said valve seat aperture as said device is lowered through said body of liquid, said valve actuator having an external portion extending upwardly along the outer surface of said barrel, said device including a keeper cooperating with said barrel for said valve member displacing movement relative thereto, said manually engageable means being located on said external portion of said actuator, and said device further including a pressure activated means operable while liquid is flowing into said barrel for indicating to the operator of said device that liquid is collecting therein.

17. A device as defined in claim 16 wherein said indicating means comprises means for providing a visual indication to the operator.

18. A device as defined in claim 16 which includes a centrally apertured closure member at the upper end of said barrel and wherein said indicating means comprises a rectilinearly displaceable telltale extending through the aperture in said closure member and trapped in said barrel by said closure member.

19. A device as defined in claim 16 wherein said indicating means comprises a whistle-incorporating closure member fixed to the upper end of said barrel.

* * * * *

UNITED STATES PATENT AND TRADEMARK OFFICE
CERTIFICATE OF CORRECTION

PATENT NO. : 4,821,587

DATED : April 18, 1989

INVENTOR(S) : M. Maurice Rogers

It is certified that error appears in the above-identified patent and that said Letters Patent is hereby corrected as shown below:

Column 5, line 50, "NoS." should read --No.--.

Column 5, line 51, after "et al." insert --U.S. Pat. No.--.

Column 9, line 60, "member" should read --movable--.

Column 10, line 1, "the" (second occurrence) should read --a--.

Column 10, line 5, "aperture" should read --apertured--.

Column 10, line 29, after "latch" insert --movable--.

Column 10, line 41, after "comprising" insert a --:-- (colon).

Column 10, line 58, "operably" should read --operable--.

Column 11, line 17, "aperture" should read --apertured--.

Column 11, line 49, "trapper" should read --trapped--.

UNITED STATES PATENT AND TRADEMARK OFFICE
CERTIFICATE OF CORRECTION

PATENT NO. : 4,821,587

DATED : April 18, 1989

INVENTOR(S) : M. Maurice Rogers

It is certified that error appears in the above-identified patent and that said Letters Patent is hereby corrected as shown below:

Column 12, line 23, "operably" should read --operable--.

Signed and Sealed this

Thirtieth Day of April, 1991

Attest:

HARRY F. MANBECK, JR.

Attesting Officer

Commissioner of Patents and Trademarks